(12) United States Patent
Shingai et al.

(10) Patent No.: US 6,452,040 B2
(45) Date of Patent: Sep. 17, 2002

(54) PRODUCTION PROCESS FOR HYDROXYALKYL (METH)ACRYLATE

(75) Inventors: Yasuhiro Shingai; Sei Nakahara; Yukihiro Yoneda; Masakazu Asami; Masatoshi Ueoka, all of Himeji (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/779,205

(22) Filed: Feb. 8, 2001

(30) Foreign Application Priority Data

Mar. 13, 2000 (JP) .................................... 2000-069541

(51) Int. Cl.⁷ .............................................. C07C 67/26
(52) U.S. Cl. ...................................................... 560/209
(58) Field of Search ........................................ 560/209

(56) References Cited

U.S. PATENT DOCUMENTS

| | | | | |
|---|---|---|---|---|
| 3,948,978 A | * | 4/1976 | Distler et al. | 260/486 |
| 4,365,081 A | * | 12/1982 | Shimizu et al. | 560/209 |
| 4,404,395 A | * | 9/1983 | Markiewitz | 560/209 |
| 4,910,329 A | | 3/1990 | McDade | |

FOREIGN PATENT DOCUMENTS

| | | |
|---|---|---|
| JP | 52-38534 B | 9/1977 |
| JP | XP-002169219 | 2/1981 |
| JP | 56-18938 A | 2/1981 |
| JP | 6-720 * | 1/1986 |
| JP | 6-720 B2 | 1/1994 |

* cited by examiner

*Primary Examiner*—Mukund J. Shah
*Assistant Examiner*—Zachary C. Tucker
(74) *Attorney, Agent, or Firm*—Haugen Law Firm PLLP

(57) ABSTRACT

The present invention provides a production process for a hydroxyalkyl (meth)acrylate which process enables to maintain the oxygen concentration of a gas phase portion of a reactor within a specific low concentration range in any stage of before adding raw materials, during the reaction, and after the reaction. The production process comprises the step of carrying out a reaction between (meth)acrylic acid and an alkylene oxide in the presence of a catalyst in order to produce the hydroxyalkyl (meth)acrylate, wherein an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % (1) before adding the alkylene oxide or (2) during the above reaction or (3) between the completion of the above reaction and the charge for the next reaction. In addition, another production process comprises the step of carrying out a reaction between (meth)acrylic acid and an alkylene oxide in the presence of a catalyst in order to produce the hydroxyalkyl (meth)acrylate, wherein the oxygen concentration of a gas phase portion of a reactor is maintained in the range of 0.1 to 14 vol % throughout the production steps.

6 Claims, No Drawings

PRODUCTION PROCESS FOR HYDROXYALKYL (METH)ACRYLATE

BACKGROUND OF THE INVENTION

A. TECHNICAL FIELD

The present invention relates to a production process for a hydroxyalkyl (meth)acrylate which comprises the step of carrying out a reaction between (meth)acrylic acid and an alkylene oxide.

B. BACKGROUND ART

An alkylene oxide forms an explosive mixed gas under certain conditions in the presence of oxygen. Therefore, when a hydroxyalkyl (meth)acrylate is produced by carrying out a reaction between (meth)acrylic acid and the alkylene oxide, it is desirable that this production is carried out under an atmosphere in which oxygen does not exist in consideration of safety. On the other hand, however, raw materials or products polymerize under an atmosphere in which oxygen does not exist at all. Therefore, it is proposed to carry out the production under an atmosphere of a gas which contains oxygen as a polymerization inhibitor.

However, when the production is carried out under an atmosphere of a mixed gas which contains oxygen in a comparatively high concentration such as air, there is a particularly high possibility that an explosive mixed gas might be formed when adding the alkylene oxide into a reactor, therefore such production is very dangerous.

In addition, when the production is carried out under an atmosphere of a mixed gas which contains oxygen in a comparatively low concentration, an inert gas (e.g. nitrogen) (which is a sealing gas (e.g. a pressured or replaced sealing gas for such as a raw material storage tank)) or oxygen is dissolved in the raw materials such as the (meth)acrylic acid and the alkylene oxide, therefore, every time these raw materials are added, the oxygen concentration of a gas phase portion of the reactor varies and, if the oxygen concentration becomes high, there occurs a danger of explosion and, if the oxygen concentration lowers near 0 vol %, there occurs a possibility of polymerization. In addition, there is a case where the oxygen concentration of the gas phase portion of the reactor varies also in the progress of the reaction.

SUMMARY OF THE INVENTION

A. OBJECT OF THE INVENTION

An object of the present invention is to provide a production process for a hydroxyalkyl (meth)acrylate wherein, when a reaction between (meth)acrylic acid and an alkylene oxide is carried out to produce the hydroxyalkyl (meth) acrylate, the process enables to maintain the oxygen concentration of a gas phase portion of a reactor within a specific low concentration range in any stage of before adding raw materials, during the reaction, and after the reaction.

B. DISCLOSURE OF THE INVENTION

The present inventors diligently studied to solve the abovementioned problems. As a result, the inventors have hit on an idea that, if a mixed gas, having an oxygen concentration as beforehand adjusted into a specific low concentration range, and/or an inert gas is used to make a concentration adjustment to maintain the oxygen concentration of a gas phase portion of a reactor within a specific low concentration range before adding raw materials, during the reaction, or after the reaction, then the above-mentioned problems can be solved. The present invention has been completed in this way.

That is to say, a production process for a hydroxyalkyl (meth)acrylate, according to the present invention, comprises the step of carrying out a reaction between (meth) acrylic acid and an alkylene oxide in the presence of a catalyst in order to produce the hydroxyalkyl (meth)acrylate, wherein an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % before adding the alkylene oxide.

In addition, another production process for a hydroxyalkyl (meth)acrylate, according to the present invention, comprises the step of carrying out a reaction between (meth)acrylic acid and an alkylene oxide in the presence of a catalyst in order to produce the hydroxyalkyl (meth) acrylate, wherein an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % during the above reaction.

In addition, yet another production process for a hydroxyalkyl (meth)acrylate, according to the present invention, comprises the step of carrying out a reaction between (meth)acrylic acid and an alkylene oxide in the presence of a catalyst in order to produce the hydroxyalkyl (meth) acrylate, wherein an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % between completion of the above reaction and charge for the next reaction.

In addition, yet another production process for a hydroxyalkyl (meth)acrylate, according to the present invention, comprises the step of carrying out a reaction between (meth)acrylic acid and an alkylene oxide in the presence of a catalyst in order to produce the hydroxyalkyl (meth) acrylate, wherein the oxygen concentration of a gas phase portion of a reactor is maintained in the range of 0.1 to 14 vol % throughout the production steps.

These and other objects and the advantages of the present invention will be more fully apparent from the following detailed disclosure.

DETAILED DESCRIPTION OF THE INVENTION

First, the production process for a hydroxyalkyl (meth) acrylate to which the characteristic production process according to the present invention is preferably applicable is roughly explained as follows.

First, a reaction between (meth)acrylic acid and an alkylene oxide is carried out in the presence of a catalyst. The conversion in this reaction is often less than 100%, therefore generally such as an unreacted residue of the (meth)acrylic acid or alkylene oxide is present in the resultant reaction liquid at the end of the reaction. Thus, the above resultant reaction liquid is led to the step to remove such as these unreacted residues of the raw materials from the reaction liquid, and then purified by such as distillation as the subsequent final step, with the result that the aimed hydroxyalkyl (meth)acrylate is obtained.

The production process according to the present invention involves controlling the atmosphere of the gas phase portion of the reactor in the above-mentioned series of production steps.

The alkylene oxide, usable in the present invention, preferably has 2 to 6 carbon atoms, more preferably 2 to 4 carbon atoms. Examples thereof include ethylene oxide, propylene oxide, and butylene oxide. Among them, ethylene oxide or propylene oxide is preferable. In addition, the (meth)acrylic acid, as used in the present invention, means acrylic acid or methacrylic acid.

The catalyst, usable for the reaction in the present invention, is not especially limited, but preferable examples thereof include at least one member selected from the group consisting of: chromium compounds such as chromium chloride, chromium acetylacetonate, chromium formate, chromium acrylate, chromium methacrylate, sodium dichromate, and chromium dibutyldithiocarbamate; iron compounds such as iron powder, iron chloride, iron formate, iron acrylate, and iron methacrylate; and amine compounds such as trialkylamines, cyclic amines (e.g. pyridine) and their quaternary salts, and resins having a basic functional group (e.g. tertiary amino groups, quaternary ammonium salts, and pyridinium groups).

The amount of the above catalyst is not especially limited, but, in the case where the catalyst is a homogeneous catalyst, the catalyst is usually used in the range of 0.05 to 10 weight %, particularly preferably 0.1 to 3 weight %, of the raw (meth)acrylic acid. In addition, in the case where the catalyst is a heterogeneous catalyst, the catalyst is usually used in the range of 5 to 50 weight %, particularly preferably 10 to 30 weight %, of the raw (meth)acrylic acid.

In addition, polymerization inhibitors may be added to the reaction liquid if necessary. Examples thereof include: phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; paraphenylenediamines such as N-isopropyl-N'-phenyl-para-phenylenediamine, N-(1,3-dimethylbutyl)-N'-phenyl-para-phenylenediamine, N-(1-methylheptyl)-N'-phenyl-para-phenylenediamine, N,N'-diphenyl-para-phenylenediamine, and N,N'di-2-naphthyl-para-phenylenediamine; amine compounds such as thiodiphenylamine and phenothiazine; copper dialkyldithiocarbamates such as copper dibutyldithiocarbamate, copper diethyldithiocarbamate, and copper dimethyldithiocarbamate; nitroso compounds such as nitrosodiphenylamine, isoamyl nitrite, N-nitrosocyclohexylhydroxylamine, N-nitroso-N-phenyl-N-hydroxylamine, and their salts; and N-oxyl compounds such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5) decane-6-oxyl, 2,2,6,6-tetramethyl-4-acetoxypiperidine-1-oxyl, and 2,2,6,6-tetramethyl-4-benzoyloxypiperidine-1-oxyl.

When the present invention is carried out, the amount of raw materials as charged for the above reaction between the (meth)acrylic acid and the alkylene oxide is such that the alkylene oxide is preferably in the range of 1.0 to 5.0 mols, more preferably in the range of 1.0 to 3.0 mols, still more preferably in the range of 1.0 to 2.0 mols, per 1 mol of the (meth)acrylic acid. In the case where the amount of the alkylene oxide as charged is smaller than 1.0 mol, there are disadvantages in that the conversion is so low as to increase the by-products. In addition, in the case where the amount of the alkylene oxide as charged is larger than 5 mols, there are economical disadvantages.

In the present invention, the reaction between the (meth) acrylic acid and the alkylene oxide in the presence of the catalyst can be carried out by methods which are used conventionally for this kind of reaction. For example, in the case where the reaction is carried out in a batch manner, the reaction is carried out by introducing the alkylene oxide into the (meth)acrylic acid. The (meth)acrylic acid may be dissolved into a solvent, and then the alkylene oxide may be introduced into the resultant solution. In this batch manner, the alkylene oxide may be added all at once, or continuously or intermittently. And in the case where the alkylene oxide is added continuously or intermittently, it is permissible that, as is often the case with this kind of reaction, the reaction is continued still after the end of the introduction of the alkylene oxide, in other words, aging is carried out, thereby completing the reaction. In addition, the (meth)acrylic acid does not need to be charged all at once in the initial stage, either, but can be added after being divided into some portions. In addition, in the case where the reaction is carried out in a continuous manner, the reaction is carried out by continuously adding the (meth)acrylic acid and the alkylene oxide into a reactor such as tubular or tank reactor and continuously extracting the resultant reaction liquid from the reactor. In this continuous manner, the catalyst may continuously be supplied together with raw materials and then continuously be extracted together with the resultant reaction liquid and, in the case of a reactor such as tubular reactor, a solid catalyst may be used in a state filled in the reactor, in other words, in what is called a fixed bed manner. In addition, in the case of the tank reactor, a solid catalyst may be used in a state fluidized together with the reaction liquid in the reactor, in other words, in what is called a fluidized bed manner. In the cases of these continuous reactions, a part of the reaction liquid may be circulated. The reaction temperature is usually in the range of preferably 40 to 130° C., more preferably 50 to 100° C. In the case where the reaction temperature is lower than 40° C., there are disadvantages in that the reaction rate is so slow as to be apart from a practical use level. On the other hand, in the case where the reaction temperature is higher than 130° C., there are disadvantages in that a large amount of by-products are formed, or in that, because the raw (meth)acrylic acid has an unsaturated double bond, such as polymerization of this (meth)acrylic acid or its product hydroxyalkyl (meth) acrylate occurs. In addition, the reaction may be carried out in a solvent for the purpose of, for example, mildly running the reaction. As to the solvent, conventional ones such as toluene, xylene, heptane, and octane are usable. The inside pressure of the reaction system during the reaction depends on the kinds or mixing ratios of the raw materials, but is generally higher than atmospheric pressure.

In the production process, according to the present invention, an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % (1) before adding the alkylene oxide or (2) during the above reaction or (3) between the completion of the above reaction and the charge for the next reaction. Hereinafter, these characteristics are explained in detail.

As is aforementioned, the alkylene oxide forms an explosive mixed gas under certain conditions in the presence of oxygen. On the other hand, however, raw materials or products polymerize under an atmosphere in which oxygen does not exist at all. Therefore, it is desirable to carry out the production under an atmosphere of a gas which contains oxygen as a polymerization inhibitor.

However, when the production is carried out under an atmosphere of a mixed gas which contains oxygen in a comparatively high concentration such as air, there is a particularly high possibility that an explosive mixed gas might be formed when adding the alkylene oxide into a reactor, therefore such production is very dangerous.

Thus, the present inventors studied what oxygen concentration range enables to prevent the formation of the explosive mixed gas and further the polymerization. As a result, the inventors have found that, if the oxygen concentration of the gas phase portion of the reactor can be maintained in the range of 0.1 to 14 vol %, then the above-mentioned object can be achieved. The above oxygen concentration is preferably in the range of 0.3 to 12 vol %, more preferably 0.5 to 8 vol %.

On the other hand, an inert gas (e.g. nitrogen) (which is a sealing gas (e.g. a pressured or replaced sealing gas for such as a raw material storage tank)) or oxygen is dissolved in the raw materials such as the (meth)acrylic acid and the alkylene oxide. Therefore, every time these raw materials are added, the oxygen concentration of a gas phase portion of the reactor varies and, if the oxygen concentration becomes high, there occurs a danger of explosion and, if the oxygen concentration lowers near 0 vol %, there occurs a possibility of polymerization. In addition, there is a case where the oxygen concentration of the gas phase portion of the reactor varies also in the progress of the reaction.

Therefore, a method is necessary by which method the preferable oxygen concentration range of 0.1 to 14 vol % can be maintained even if the variation of the oxygen concentration is caused by such as the above-mentioned factors. The present inventors studied and, as a result, have found that the oxygen concentration of the gas phase portion of the reactor can be maintained in the range of 0.1 to 14 vol % by using the inert gas and/or the mixed gas of oxygen and the inert gas with a beforehand adjusted oxygen concentration of 0.1 to 14 vol % and adding these gases correspondingly to the variation of the oxygen concentration of the gas phase portion of the reactor in order to adjust this oxygen concentration.

Namely, before the alkylene oxide is added, the raw (meth)acrylic acid is beforehand charged into the reactor, but there can occur a case where, even if the oxygen concentration of the gas phase portion of the reactor is adjusted in the range of 0.1 to 14 vol % before the charge of the (meth)acrylic acid, the oxygen concentration of the gas phase portion of the reactor varies due to the charge of the (meth)acrylic acid, because the aforementioned sealing gas is dissolved in the (meth)acrylic acid. Thus, the inert gas and/or the mixed gas of oxygen and the inert gas with a beforehand adjusted oxygen concentration of 0.1 to 14 vol % is added into the gas phase portion of the reactor correspondingly to the variation of the oxygen concentration of the gas phase portion of the reactor in order to adjust this oxygen concentration. Specifically, for example, when the oxygen concentration of the gas phase portion of the reactor increases, the inert gas is added in order to decrease this oxygen concentration, or otherwise, when the oxygen concentration of the gas phase portion of the reactor decreases, the mixed gas of oxygen and the inert gas with a beforehand adjusted oxygen concentration of 0.1 to 14 vol % is added in order to increase this oxygen concentration, thus maintaining the oxygen concentration of the gas phase portion of the reactor in the range of 0.1 to 14 vol %. Furthermore, for example, when the inert gas has excessively been added for the oxygen concentration adjustment, there is also a case where the oxygen concentration of the gas phase portion of the reactor is adjusted in the range of 0.1 to 14 vol % again by adding the mixed gas of oxygen and the inert gas with a beforehand adjusted oxygen concentration of 0.1 to 14 vol %.

Furthermore, during the reaction after adding the alkylene oxide, there can occur a case where, even if the oxygen concentration of the gas phase portion of the reactor is adjusted in the range of 0.1 to 14 vol % before the addition of the alkylene oxide, the oxygen concentration of the gas phase portion of the reactor varies due to the addition of the alkylene oxide, because the aforementioned sealing gas is dissolved also in the added alkylene oxide. Furthermore, in the case of using the iron powder which is effective for the present reaction (JP-B-038534/1977), the iron powder grows oxidized into divalent or trivalent iron ion during the reaction, when oxygen in the reactor is consumed. Hence, there can occur a case where the oxygen concentration of the gas phase portion of the reactor varies due to such a factor as well. Thus, the inert gas and/or the mixed gas of oxygen and the inert gas with a beforehand adjusted oxygen concentration of 0.1 to 14 vol % is added into the gas phase portion of the reactor correspondingly to the variation of the oxygen concentration of the gas phase portion of the reactor in order to adjust this oxygen concentration. Specifically, similarly to the aforementioned, for example, when the oxygen concentration of the gas phase portion of the reactor increases, the inert gas is added in order to decrease this oxygen concentration, or otherwise, when the oxygen concentration of the gas phase portion of the reactor decreases, the mixed gas of oxygen and the inert gas with a beforehand adjusted oxygen concentration of 0.1 to 14 vol % is added in order to increase this oxygen concentration, thus maintaining the oxygen concentration of the gas phase portion of the reactor in the range of 0.1 to 14 vol %. Furthermore, for example, when the inert gas has excessively been added for the oxygen concentration adjustment, there is also a case where the oxygen concentration of the gas phase portion of the reactor is adjusted in the range of 0.1 to 14 vol % again by adding the mixed gas of oxygen and the inert gas with a beforehand adjusted oxygen concentration of 0.1 to 14 vol %.

In addition, similarly also in the case where the reaction is continuously carried out, the oxygen concentration of the gas phase portion of the reactor varies due to factors such as influence of the sealing gas which is dissolved in the alkylene oxide and the (meth)acrylic acid that are continuously supplied into the reactor. Therefore, the production process according to the present invention is useful similarly to the above.

The reaction liquid is discharged from the reactor after the end of the reaction, but the internal pressure of the reactor falls then, so there can occur necessity to inject a gas from the outside in order to prevent this internal pressure falling. In addition, there is also a case where, when the reaction liquid is discharged from the reactor, the reaction liquid is discharged by the gas injection from the outside all along. In these operations, the oxygen concentration of the gas phase portion of the reactor can vary during the gas injection from the outside. In addition, if the oxygen concentration of the gas which is injected from the outside is high, there is a very great danger that an explosive gas might be formed in the case where the alkylene oxide remains in the reactor. Thus, the oxygen concentration of the gas phase portion of the reactor is maintained in the range of 0.1 to 14 vol % using the inert gas and/or the mixed gas of oxygen and the inert gas with a beforehand adjusted oxygen concentration of 0.1 to 14 vol % as the gas which is used when the above-mentioned operations are carried out. Furthermore, if, also between the discharge of the reaction liquid and the charge for the next reaction, the inert gas and/or the mixed gas of oxygen and the inert gas with a beforehand adjusted oxygen concentration of 0.1 to 14 vol % is used to carry out the adjustment to maintain the oxygen concentration of the gas phase portion of the reactor in the range of 0.1 to 14 vol %, then there are advantages of enabling to retain the reactor in a safe state where there is only a low possibility that the alkylene oxide remaining in the reactor might mix with oxygen to form an explosive mixed gas, and where there occurs no polymerization of the residual reaction liquid (which exists in such as valve and nozzle portions) in the reactor.

As to specific methods for controlling the oxygen concentration of the gas phase portion of the reactor, the inert gas and/or the mixed gas of oxygen and the inert gas may be added either continuously or intermittently. In addition, these gases may be added into the gas phase portion of the reactor, or may be added into the reaction liquid. In either case, for example, a plate for dispersion may be placed in order to improve the gas dispersibility.

In addition, there is a case where the inside pressure of the reactor rises due to the addition of these gases. In such a case, the gases may intermittently be purged, or may continuously be purged if the gases are continuously added.

The inside pressure of the reactor is preferably in the range of 0.1 to 1 MPa, more preferably 0.1 to 0.7 MPa. In the case where the inside pressure of the reactor is lower than 0.1 MPa, it is difficult for the alkylene oxide to exist in a liquid state under reaction temperature conditions, so the reaction rate is slow. In addition, in the case where the inside pressure of the reactor is higher than 1 MPa, there are economical disadvantages of needing a high pressure-resistant reactor.

In addition, the alkylene oxide which is contained in gases as purged from the reactor, including the above purged gases, may be disposed of by being absorbed into such as water. However, there are economical advantages if the alkylene oxide is recycled after being recovered by: leading the alkylene oxide to alkylene oxide recovery facilities and then condensing the alkylene oxide with a condenser; or getting the alkylene oxide absorbed into a liquid such as a polar solvent (e.g. water), the raw (meth)acrylic acid, and the resultant hydroxyalkyl (meth)acrylate. Especially, it is preferable that the alkylene oxide is recycled after being recovered by getting the alkylene oxide absorbed into the raw (meth)acrylic acid, the resultant hydroxyalkyl (meth) acrylate, or their liquid mixture.

As is mentioned above, the production process according the invention enables to maintain the oxygen concentration of the gas phase portion of the reactor in the range of 0.1 to 14 vol % (1) before adding the alkylene oxide or (2) during the reaction or (3) between the completion of the reaction and the charge for the next reaction. This production process may be applied according to the production step that involves a large variation of the oxygen concentration of the gas phase portion of the reactor. Namely, for example, in the case where the variation of the oxygen concentration of the gas phase portion of the reactor because of the charge of the raw (meth)acrylic acid is large, a production process according to the present invention may be applied in which production process an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % before adding the alkylene oxide. In the case where the variation of the oxygen concentration of the gas phase portion of the reactor because of the addition of the alkylene oxide is large, another production process according to the present invention may be applied in which production process an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % during the reaction. In the case where the variation of the oxygen concentration of the gas phase portion of the reactor in the step of discharging the resultant reaction product is large, another production process according to the present invention may be applied in which production process an inert gas and/or a mixed gas of oxygen and an inert gas with a beforehand adjusted oxygen concentration of 0.1 to 14 vol % is used to maintain the oxygen concentration of a gas phase portion of a reactor in the range of 0.1 to 14 vol % between the completion of the reaction and the charge for the next reaction.

Furthermore, as to the production process according to the present invention for the hydroxyalkyl (meth)acrylate, it can be said to be a preferred mode that the oxygen concentration of the gas phase portion of the reactor is maintained in the range of 0.1 to 14 vol % throughout the production steps. The reason therefor is that, if such a low oxygen concentration can be maintained throughout the production steps, then safe and stable production can be actualized.

In addition, the production process for the hydroxyalkyl (meth)acrylate generally comprises a reaction step, a separation step for an unreacted residue of the alkylene oxide, a separation step for an unreacted residue of the (meth)acrylic acid, and a distillation step for the reaction product, wherein the separation step for an unreacted residue of the (meth) acrylic acid might be omitted if the conversion of the (meth)acrylic acid in the reaction is near 100%.

The above separation step for an unreacted residue of the alkylene oxide, for example, means a step in which: the unreacted residue of the alkylene oxide is separated and removed from the resultant reaction liquid by utilizing such as an inert gas with a packing column, and then the alkylene oxide included in the resultant gas is absorbed into a solvent such as water, whereby the unreacted residue of the alkylene oxide is disposed of or recovered for recycling.

The above separation step for an unreacted residue of the (meth)acrylic acid, for example, means a step in which: the unreacted residue of the (meth)acrylic acid is separated and removed from the resultant reaction liquid by distillation with an apparatus, and then the resultant vapor of the (meth)acrylic acid is condensed with such as a condenser or absorbed into a solvent such as water, whereby the unreacted residue of the (meth)acrylic acid is disposed of or recovered for recycling.

The above distillation step for the reaction product, for example, means a step in which: the reaction product is distilled by distillation with an apparatus and then condensed with such as a condenser, whereby a product is obtained.

Then, as to the production process according to the present invention for the hydroxyalkyl (meth)acrylate, it is a more preferred mode that the oxygen concentration is maintained in the range of 0.1 to 14 vol % not only in the gas phase portion of the reactor, but also in a gas phase portion in the step of separating an unreacted residue of the alkylene oxide from the resultant reaction product, namely, as to the aforementioned example, as follows: a gas phase portion in the packing column; a gas phase portion such as a vapor line through which a gas led from the packing column is passed till being absorbed into a solvent such as water; and a gas phase portion of an intermediate tank such as a feed tank which is appended to the packing column.

A still more preferred mode is that the oxygen concentration is maintained in the range of 0.1 to 14 vol % also in a gas phase portion in the step of separating an unreacted residue of the (meth)acrylic acid from the resultant reaction product, namely, as to the aforementioned example, as follows: a gas phase portion in the apparatus; a gas phase portion such as a vapor line through which a vapor led from the apparatus is passed till being condensed with such as a condenser or absorbed into a solvent such as water; and a gas phase portion of an intermediate tank such as a feed tank and a distillate tank which are appended to the apparatus; and/or in a gas phase portion in the distillation step for the reaction product, namely, as to the aforementioned example, as follows: a gas phase portion in the apparatus; a gas phase portion such as a vapor line through which a vapor led from the apparatus is passed till being condensed with such as a condenser; and a gas phase portion of an intermediate tank such as a feed tank and a distillate tank which are appended to the apparatus.

Herein, equipments which are used in the separation step for the unreacted residue of the alkylene oxide or (meth)acrylic acid and the distillation step for the reaction product are not especially limited, but examples thereof include packing columns, plate columns, bubble cap tray columns, and apparatuses.

If the oxygen concentration of the above gas phase portions in the step of separating the unreacted residue of the alkylene oxide from the resultant reaction product, other than the gas phase portion of the reactor, is also maintained in the range of 0.1 to 14 vol %, then there is only a low possibility that a gas in such gas phase portions might mix with the alkylene oxide to form an explosive mixed gas, and further, no polymer forms in the separation step for the unreacted residues of the raw materials and the distillation step for the reaction product, therefore safely the hydroxyalkyl (meth)acrylate can be produced.

Incidentally, in the case where a gas having a high oxygen concentration (e.g. air) is used as an oxygen source instead of the inert gas and/or the mixed gas of oxygen and the inert gas with a beforehand adjusted oxygen concentration of 0.1 to 14 vol % which are used in the present invention, there is a high possibility that an explosive gas having a high oxygen concentration might be formed locally, for example, near an air injection nozzle, even if the oxygen concentration of the entirety of the gas phase portion of the reactor is within the range of 0.1 to 14 vol % as defined in the present invention.

Effects and Advantages of the Invention

When a reaction between (meth)acrylic acid and an alkylene oxide is carried out to produce a hydroxyalkyl (meth)acrylate, the process according to the present invention enables to maintain the oxygen concentration of a gas phase portion of a reactor within a specific low concentration range in any stage of before adding raw materials, during the reaction, and after the reaction.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples of some preferred embodiments. Incidentally, hereinafter, unless otherwise noted, the unit "%" of the oxygen and nitrogen concentrations is "vol %".

EXAMPLE 1

The inside gas of an autoclave of 2 liters in capacity, as equipped with a thermometer, a heating and cooling unit, and a stirrer, was replaced with a mixed gas which had been adjusted so as to have an oxygen concentration of 3% and a nitrogen concentration of 97%. Then, 844 g of acrylic acid was charged from a vessel (containing raw acrylic acid and having been sealed in an oxygen concentration of 7% and a nitrogen concentration of 93%) through piping (as fitted to the autoclave) into the autoclave by use of a feed pump, and then 2 g of phenothiazine, 5 g of hydroquinone monomethyl ether (both as polymerization inhibitors), and 5 g of chromium acetate (as a catalyst) were added into the autoclave.

At this time, the oxygen concentration of a gas phase portion of the autoclave was 5% under the influence of oxygen as dissolved in the raw acrylic acid. Next, the inside liquid temperature of the autoclave was raised to 70° C. which was a reaction temperature. Thereafter, the oxygen concentration in the autoclave was adjusted to 3.5% with nitrogen gas. In addition, the inside pressure of the autoclave was adjusted to 0.03 MPa. Then, 620 g of ethylene oxide was supplied from a high pressure-resistant vessel (containing the ethylene oxide and having been sealed at 0.5 MPa with a gas having a nitrogen concentration of 100%) through piping (as fitted to the autoclave) into the inside liquid of the autoclave at almost a constant rate by use of a feed pump over a period of about 4 hours, while the reaction was carried out with the temperature maintained at 70° C. After the supply of the ethylene oxide had ended, the oxygen concentration of the gas phase portion of the autoclave lowered to 2.0% under the influence of nitrogen as dissolved in the raw ethylene oxide and the influence of an unreacted gas of the alkylene oxide. Thereafter, the reaction was continued for 3 hours with the temperature maintained at 70° C. At this time, the oxygen concentration of the gas phase portion of the autoclave was 2.5% because the amount of the unreacted gas of the alkylene oxide decreased in comparison with what it had been after the supply end of the raw ethylene oxide. Hereupon, the resultant reaction liquid was analyzed, so that the acrylic acid concentration was 0.05 wt %. Therefore, the autoclave was cooled at once, and then the reaction liquid was discharged by utilizing the residual inside pressure of the autoclave. On its way, a mixed gas which had been adjusted so as to have an oxygen concentration of 3% and a nitrogen concentration of 97% was fitly injected so that the residual inside pressure of the reactor might not be 0.1 MPa or lower.

After the above discharge of the reaction liquid had ended, the inside gas of the autoclave was purged to replace it with a mixed gas which had been adjusted so as to have an oxygen concentration of 3% and a nitrogen concentration of 97%. Hereinafter, the same reaction operation as the above was repeated 30 times, while no polymer was observed in the discharged reaction liquid. In addition, after these 30-time repeats of the reaction operation had ended, the autoclave was opened to inspect the inside of the autoclave. However, no polymer formation was observed.

EXAMPLE 2

The inside gas of an autoclave of 1 liter in capacity, as equipped with a thermometer, a heating and cooling unit, and a stirrer, was replaced with a mixed gas which had been adjusted so as to have an oxygen concentration of 4.5% and a nitrogen concentration of 95.5%. Then, a mixture of which the total amount was 600 ml was prepared by charging this autoclave with 400 ml of a water-humidified basic anion-exchange resin (DIAION PA316 produced by Mitsubishi Chemical Corporation) (as a catalyst) and with acrylic acid by supplying it from a vessel (containing raw acrylic acid (in which phenothiazine and hydroquinone monomethyl ether were dissolved in the ratios of 0.2 wt % and 0.5 wt % respectively as polymerization inhibitors) and having been sealed in an oxygen concentration of 7% and a nitrogen concentration of 93%) through piping (as fitted to the autoclave) into the autoclave by use of a feed pump. At this time, the oxygen concentration of a gas phase portion of the autoclave was 6% under the influence of oxygen as dissolved in the raw acrylic acid. Next, the inside liquid temperature of the autoclave was raised to 70° C. which was a reaction temperature. Thereafter, the oxygen concentration in the autoclave was adjusted to 4% with nitrogen gas. In addition, the inside pressure of the autoclave was adjusted to 0.03 MPa. Then, the above acrylic acid in which the polymerization inhibitors were dissolved was continuously supplied into the autoclave at a rate of 109 g/h, and further, ethylene oxide was continuously supplied from a high pressure-resistant vessel (containing the ethylene oxide and having been sealed at 0.5 MPa with a gas having a nitrogen concentration of 100 %) through piping (as fitted to the autoclave) into the inside liquid of the autoclave at a rate of 101 g/h by use of a feed pump. The resultant reaction liquid was continuously discharged such that the liquid level in the autoclave could be fixed during the reaction. After 60 hours, the oxygen concentration of the gas phase portion of the autoclave lowered to 1.3% under the influence of nitrogen as dissolved in the raw ethylene oxide and the influence of an unreacted gas of the alkylene oxide. Therefore, the oxygen concentration of the gas phase portion of the autoclave was changed to 3% with a mixed gas which had been adjusted so as to have an oxygen concentration of 4.5% and a nitrogen concentration of 95.5%. Still thereafter, the oxygen concentration of the gas phase portion of the autoclave was monitored and adjusted with the mixed gas (which had been adjusted so as to have an oxygen concentration of 4.5% and a nitrogen concentration of 95.5%) in order that the oxygen concentration might not be 0.1% or lower. On the other hand, the inside gas of the autoclave was fitly purged so that the inside pressure of the autoclave could be in the range of 0.1 to 1 MPa. The reaction was continuously carried out for 200 hours in this state, while no polymer was however observed in the discharged reaction liquid. In addition, the reaction liquid was cooled, and then the autoclave was opened to inspect the inside of the autoclave. However, no polymer formation was observed.

In addition, the reaction liquid as obtained in a stationary state was analyzed by gas chromatography, so that the conversion of the acrylic acid was 86%.

COMPARATIVE EXAMPLE 1

The reaction was carried out in the same way as of Example 1 except that, before the supply of the ethylene oxide, the gas phase portion of the autoclave was adjusted so as to have a nitrogen concentration of 100% (oxygen concentration=0%) instead of being adjusted so as to have an oxygen concentration of 3.5%. After the supply of the ethylene oxide had been completed, the reaction liquid was sampled, so that a fine polymer was observed in the reaction liquid. Therefore, the reaction was discontinued, and then the reaction liquid was cooled. Thereafter, the inside of the autoclave was inspected, so that a filmy polymer was observed in the gas phase portion of the autoclave, and that a small amount of fine polymer particles were observed in the reaction liquid as well.

COMPARATIVE EXAMPLE 2

The reaction was carried out in the same way as of Example 1 except that the inside gas of the autoclave was replaced with a gas having a nitrogen concentration of 100% (oxygen concentration=0%) after the discharge of the reaction liquid had ended. When the 20th-time reaction operation had ended, the inside of the autoclave was inspected, so that a polymer was observed in gas phase portions of the autoclave, particularly, thermometer protector tubes, nozzle portions of such as pressure gauges.

COMPARATIVE EXAMPLE 3

An attempt was made to carry out the reaction in the same way as of Example 1 except that the oxygen concentration of the gas phase portion of the autoclave was adjusted by supplying nitrogen and air separately from each other instead of using the mixed gas which had been adjusted so as to have an oxygen concentration of 3% and a nitrogen concentration of 97%. However, when air was supplied following nitrogen, the oxygen concentration near a nozzle for supplying this air was measured to show 16%, so there was a danger of explosion. Thus, the reaction was discontinued.

COMPARATIVE EXAMPLE 4

The reaction was carried out in the same way as of Example 2 except that the oxygen concentration in the autoclave was changed to 1% after heating the acrylic acid to 70° C. After 150 hours from the end of the continuous addition of the acrylic acid and the ethylene oxide, the oxygen concentration of the gas phase portion of the autoclave was measured. The result showed a concentration reduction to 0.05%, so the reaction was discontinued at once. The reaction liquid was cooled, and then the autoclave was opened to inspect the inside of the autoclave. As a result, attachment of a polymer to the gas phase portion of the autoclave was seen.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl (meth) acrylate, which comprises the steps of,
    a) carrying out a reaction between (meth)acrylic acid and an alkylene oxide in the presence of a catalyst in order to produce said hydroxyalkyl (meth)acrylate;
    b) wherein an inert gas or a mixed gas of oxygen and an inert gas is used to maintain the oxygen concentration of a gas phase portion of a reactor in the range of 0.1 to 14 vol % from a completion of said reaction to a charge for the next reaction; and
    c) wherein, in the case of using a mixed gas of oxygen and an inert gas, said mixed gas has a beforehand adjusted oxygen concentration of 0.1 to 14 vol %.

2. A production process according to claim 1, which further comprises the step of, after said completion of the reaction, discharging the resultant reaction liquid under pressure while said maintenance of the oxygen concentration of the gas phase portion of the reactor is carried out.

3. A production process according to claim 1, wherein the catalyst is at least one member selected from the group consisting of iron compounds, chromium compounds, and amine compounds.

4. A production process according to claim 2, wherein the catalyst is at least one member selected from the group consisting of iron compounds, chromium compounds, and amine compounds.

5. A production process for a hydroxyalkyl (meth) acrylate, which comprises the steps of:

a) carrying out a reaction between (meth)acrylic acid and an alkylene oxide in the presence of a catalyst in a reactor in order to produce said hydroxyalkyl (meth) acrylate;

b) maintaining an oxygen concentration of a gas phase of the reactor in the range of 0.1 to 14 vol % by introducing an inert gas or a mixed gas of oxygen and an inert gas into the reactor, wherein said step of maintaining said oxygen concentration occurs before adding said alkylene oxide, wherein, in the case of introducing a mixed gas of oxygen and an inert gas, said mixed gas has an adjusted oxygen concentration of 0.1 to 14 vol % before being introduced to the reactor:

c) determining when the oxygen concentration in the gas phase of the reactor is relatively high and then introducing said inert gas or said mixed gas to the gas phase of the reactor; and d) determining when the oxygen concentration in the gas phase of the reactor is relatively low and then introducing said mixed gas to the gas phase of the reactor.

6. A production process for a hydroxyalkyl (meth) acrylate, which comprises the steps of:

a) carrying out a reaction between (meth)acrylic acid and an alkylene oxide in the presence of a catalyst in a reactor in order to produce said hydroxyalkyl (meth) acrylate;

b) maintaining an oxygen concentration of a gas phase of the reactor in the range of 0.1 to 14 vol % by introducing an inert gas or a mixed gas of oxygen and an inert gas into the reactor, wherein said step of maintaining said oxygen concentration occurs during said reaction; wherein, in the case of introducing a mixed gas of oxygen and an inert gas, said mixed gas has an adjusted oxygen concentration of 0.1 to 14 vol % before being introduced to the reactor;

c) determining when the oxygen concentration in the gas phase of the reactor is relatively high and then introducing said inert gas or said mixed gas to the gas phase of the reactor; and d) determining when the oxygen concentration in the gas phase of the reactor is relatively low and then introducing said mixed gas to the gas phase of the reactor.

* * * * *